United States Patent [19]
Imura

[11] Patent Number: 5,384,641
[45] Date of Patent: Jan. 24, 1995

[54] COLOR MEASURING INSTRUMENT WITH MULTIPLE INPUTS OF LIGHT

[75] Inventor: Kenji Imura, Toyohashi, Japan
[73] Assignee: Minolta Co., Ltd., Osaka, Japan
[21] Appl. No.: 98,630
[22] Filed: Jul. 28, 1993
[30] Foreign Application Priority Data
 Jul. 29, 1992 [JP] Japan ................................. 4-202568
[51] Int. Cl.⁶ ............................................. G01N 21/47
[52] U.S. Cl. ................................... 356/446; 250/228; 356/236
[58] Field of Search ................... 356/236, 402, 446; 250/228

[56] References Cited
U.S. PATENT DOCUMENTS
2,601,182 6/1952 Tyler ........................... 250/228 X
3,327,583 6/1967 Vanderschmidt et al. ..... 250/228 X
4,932,779 6/1990 Keane ........................... 356/236 X FOREIGN PATENT DOCUMENTS
61-233328 10/1986 Japan .
WO82/03914 11/1982 WIPO .

Primary Examiner—Vincent P. McGraw
Attorney, Agent, or Firm—Price, Gess & Ubell

[57] ABSTRACT

In the disclosed invention, a device for measuring optical properties of samples has an integrating sphere having an aperture for the placement of the sample and multiple apertures to take in light from light sources, as well as multiple light sources for illuminating the inside of said integrating sphere. As described above, by means of illumination with multiple light sources, errors due to unevenness in luminous intensity of the illuminating light do not occur, and accurate optical measurement of the sample is made possible.

15 Claims, 4 Drawing Sheets

COLOR MEASURING INSTRUMENT WITH MULTIPLE INPUTS OF LIGHT

BACKGROUND OF THE INVENTION

1. Field of the Invention

This invention relates to a device for measuring optical properties of samples, in which an integrating sphere is employed and which is applied in a spectrocolorimeter, etc.

2. Description of the Prior Art

In spectrocolorimeters using an integrating sphere and based on diffused illumination, even if they are constructed with the same geometry (d/8 type, for example), certain errors occur between units, not only of different models, but also between those of the same model.

FIG. 4 shows the construction of a conventional device for measuring optical properties of samples, as well as the luminous intensity distribution of said device.

Inner wall 1a of integrating sphere 1 is coated with white powder having high rates of diffusion and reflection. The light beam from light source 11 enters integrating sphere 1 from aperture 16. It first illuminates illuminated area 17 facing aperture 16. After it is diffused and reflected here, it becomes multi-reflected inside integrating sphere 1 and evenly illuminates sample 3 located at aperture 2 for the placement of sample 3.

The light reflected by sample 3 passes through aperture 41, converges by virtue of lens 42 and forms an image on measuring area restriction plate 43. Optical axis 49 of the reflected light is tilted eight degrees away from the normal line of sample 3, constructing so-called d/8 geometry. Aperture 43a located on measuring area restriction plate 43 determines projection 3a on sample 3 as the measurement area.

The light beam passing through aperture 43a converges by virtue of lens 44 and enters one end of optical fiber 45. The other end of optical fiber 45 is connected to a spectrometer not shown in the drawing, which calculates the spectral reflectance of sample 3.

In the above conventional device for measuring optical properties of samples, as shown in the lower half of FIG. 4, luminous intensity 4 of the light illuminating the sample at aperture 2 deviates substantially from perfect diffusion 4i. In other words, of the deviation from perfect diffusion 4i, concavity 4a is attributable to aperture 41 for the measurement and convexity 4b is attributable to the fact that the diffused reflection from directly illuminated area 17, which the light beam from light source 11 first illuminates, directly reaches aperture 2 for the placement of sample 3.

In addition, unevenness is also seen in that the intensity of light incident to the sample at narrow angles is relatively low in comparison with perfect diffusion.

As described above, the luminous intensity of the illuminating light at the sample placement aperture deviates from perfect diffusion despite the use of an integrating sphere, and moreover, this deviation is not uniform between units, regardless whether they are of different models or of the same model. This is because the location of apertures in the integrating sphere and the coating material on the inner wall may be different among different models, and slight errors in the size or location of the apertures or unevenness in coating may exist even among units of the same model.

This invention was made in consideration of the above problem. Its object is to provide a device which, when measuring the optical properties of samples, such as spectral reflectance, accurately measures optical properties of samples without any errors caused by unevenness in luminous intensity of the illuminating light.

SUMMARY OF THE INVENTION

The device for measuring optical properties of samples, in which the present invention is applied, has an integrating sphere having a sample placement aperture and apertures used to take in light from light sources. It also has light sources located at each of the apertures used for light sources, which illuminate the inside of the integrating sphere. It also has a light receiving means and a calculating means, and the calculating means calculates the optical properties of the sample based on the output from the light receiving means.

As described above, by illuminating the inside of integrating sphere 1 using multiple light sources, errors caused by unevenness in luminous intensity of the illuminating light do not occur and accurate optical measurement of the sample becomes possible.

Further, in addition to the integrating sphere having multiple apertures used to take in the light from multiple light sources and multiple light sources, the device for measuring optical properties of samples has a means which generates weighting coefficients which convert the sum of the luminous intensities of the above multiple light sources into an ideal luminous intensity. The calculating means calculates the optical properties of the sample based on the output from the light receiving means and its weighting coefficients.

As described above, by calculating the optical properties using weighting coefficients, it becomes possible to correct errors caused by unevenness in the luminous intensity of illuminating light.

Other objects and advantages of the present invention will become apparent from the detailed description to follow, taken in conjunction with the appended claims.

DETAILED DESCRIPTION OF THE PREFERRED EMBODIMENTS

Figure 1:
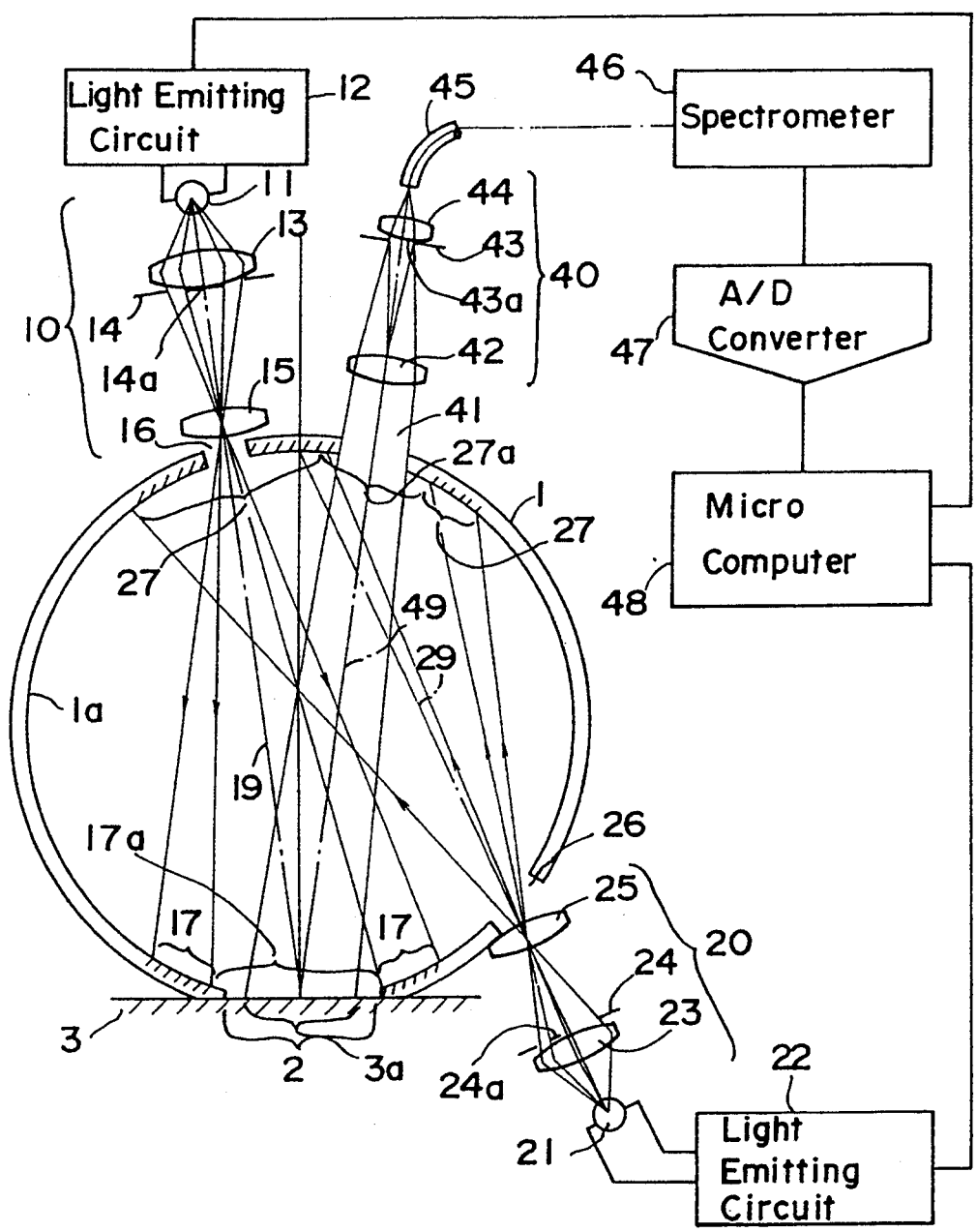
FIG. 1 is an illustration showing the construction of the first embodiment of the device for measuring optical properties of samples of the present invention.

The first embodiment of the device for measuring optical properties of samples of the present invention is described with reference to the drawings. FIG. 1 is an illustration of the construction of the device for measuring optical properties of samples of the present invention.

Integrating sphere 1 is a hollow sphere, inner wall 1a of which is coated with white diffusive reflective powder such as magnesium oxide or barium oxalate, and is used for the measurement of the sum of light beams emitted in all directions from the light source.

In addition, on integrating sphere 1 are formed aperture 16 located near the top in order to receive the light from first illumination optical system 10, aperture 26 located near the bottom in order to receive the light from second illumination optical system 20, aperture 2 located on the bottom for the illumination of sample 3, the subject of measurement, and aperture 41 near the top to guide the light reflected by sample 3 to the measuring optical system.

First illumination optical system 10 is located at aperture 16 and comprises light source 11, lenses 13 and 15 and masking plate 14. It first illuminates the inside of integrating sphere 1 near aperture 2 as directly illuminated area 17.

For light source 11, such sources as xenon flashes are used, which emit light into integrating sphere 1. Masking plate 14 is located on lens 13 on the side of integrating sphere 1 and limits the area illuminated by light source 11. In the center of masking plate 14 is formed shading unit 14a, which creates donut-shaped directly illuminated area 17 having shaded area 17a so that sample 3 is not directly illuminated.

The light beam from light source 11 converges by virtue of lens 13 and forms an image of masking plate 14 near aperture 2 of inner wall 1a via lens 15 located at the focal point of aperture 16.

Second illumination optical system 20 is located at aperture 26 and comprises light source 21, lenses 23 and 25 and masking plate 24. It first illuminates the inside integrating sphere i near the top as directly illuminated area 27.

For light source 21, such sources as xenon flashes are used, which emit light into integrating sphere 1. Masking plate 24 is located on lens 23 on the side of integrating sphere I and limits the area illuminated by light source 21. In the center of masking plate 24 is formed shading unit 24a, which creates shaded area 27a so that aperture 41 is not directly illuminated.

The light beam from light source 21 converges by virtue of lens 23 and forms an image of masking plate 24 near the top of inner wall 1a via lens 25 located at the focal point of aperture 26.

Measurement optical system 40 converges the light reflected by sample 3 and comprises lenses 42 and 44 and masking plate 43. Optical axis 49 of measurement optical system 40 is tilted eight degrees away from the normal line of the surface of sample 3. Masking plate 43 has aperture 43a at its center and limits the measurement area. Projection 3a on the surface of sample 3 becomes the measurement area by virtue of aperture 43a.

The light beams incident from first and second optical systems 10 and 20 through apertures 16 and 26 illuminate sample 3 after being multi-reflected by inner wall 1a of integrating sphere 1. The light reflected in the direction tilted eight degrees away from the normal line of the surface of sample 3 passes through aperture 41 and forms an image on masking plate 43 after converging by virtue of lens 42. The reflected light which passed through aperture 43a further converges by virtue of lens 44 and enters one end of optical fiber 45, whereby it is guided to the measuring unit of spectrometer 46, etc.

Spectrometer 46 is connected to the other end of optical fiber 45 and separates the light guided from optical fiber 45 into spectral components. Microcomputer 48 controls the operation of this device for measuring optical properties of samples, and includes a built-in control program for performing measurement, memories to save data and coefficients to be described below, and a calculation unit which carries out calculation based on the data.

Light emitting circuits 12 and 22 cause light sources 11 and 12 to emit light and operates based on instructions from microcomputer 48. Spectral data generated by spectrometer 46 are converted into digital values by A/D converter 47 and incorporated into microcomputer 48.

Figure 2A:
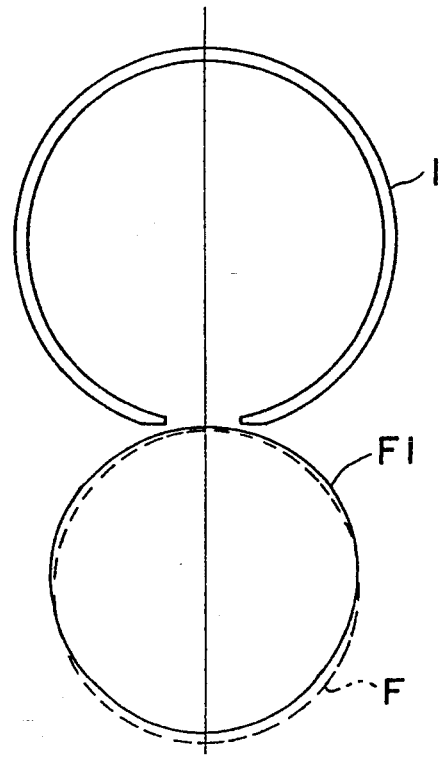
FIG. 2A is an illustration showing the luminous intensity at the center of aperture 2 by virtue of the first illumination optical system of the first embodiment.
Figure 2B:
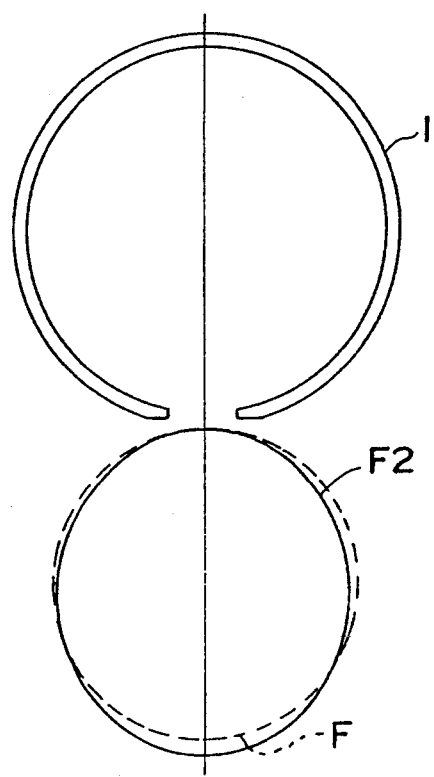
FIG. 2B is an illustration showing the luminous intensity at the center of aperture 2 by virtue of the second illumination optical system of the first embodiment.

The measurement procedure is explained below with reference to FIGS. 1, 2A and 2B. FIGS. 2A and 2B show the luminous intensities in the first embodiment: FIG. 2A shows luminous intensity F1 at the center of aperture 2 by virtue of the first illumination optical system, and FIG. 2B shows luminous intensity F2 at the center of aperture 2 by virtue of the second illumination optical system.

First, the setting of coefficients to correct luminous intensities is explained. A highly directional light receiving sensor is located at aperture 2, which measures luminous intensity.

Light emitting circuit 12 is operated and light source 11 is made to emit light. Because first illumination optical system 10 first illuminates directly illuminated area 17 of inner wall 1a of integrating sphere 1, with regard to luminous intensity F1 at aperture 2 via this optical system, light incident at narrow angles is emphasized when compared with ideal luminous intensity F, as shown in FIG. 2A.

Subsequently, light emitting circuit 22 is operated and light source 21 is made to emit light. When this happens, because second illumination optical system 20 first illuminates directly illuminated area 27 of inner wall 1a of integrating sphere 1, with regard to luminous intensity F2 at aperture 2 via this optical system, light incident at close to a right angle is emphasized when compared with ideal luminous intensity F, as shown in FIG. 2B.

Based on data regarding the light received by virtue of the light emitted by first and second illumination optical systems 10 and 20, luminous intensities F1 and F2 are measured for each wavelength, respectively.

Now, if the coefficient of first illumination optical system is $C(\lambda)$ and that of second illumination optical system 20 is $D(\lambda)$, $C(\lambda)$ and $D(\lambda)$ are determined for each wavelength such that $$C(\lambda)\cdot F1(\lambda)+D(\lambda)\cdot F2(\lambda)$$

comes closest to ideal luminous intensity $F(\lambda)$.

Coefficients $C(\lambda)$ and $D(\lambda)$ thus obtained are saved in a memory of microcomputer 48.

The measurement of samples is explained below.

First, based on instructions from microcomputer 48, light emitting circuit 12 is operated and light source 11 is made to emit light. The light reflected by sample 3 is input to spectrometer 46. The spectral data generated by spectrometer 46 are converted into digital values by A/D converter 47, after which the spectral reflectance is calculated by microcomputer 48 and is saved in one of the microcomputer's memories. The spectral reflectance of sample 3 obtained here is deemed as R1(λ).

Following the above, based on the instructions from microcomputer 48, light emitting circuit 22 is operated and light source 21 is made to emit light. The light reflected by sample 3 is input to spectrometer 46. The spectral data generated by spectrometer 46 are converted into digital values by A/D converter 47, after which the spectral reflectance is calculated by microcomputer 48 and is saved in one of the microcomputer's memories. The spectral reflectance of sample 3 obtained here is deemed R2(λ).

Next, the calculation, $$R(\lambda) = C(\lambda) \cdot R1(\lambda) + D(\lambda) \cdot R2(\lambda)$$

is carried out by the calculation unit of microcomputer 48 based on coefficients C(λ) and D(λ) saved in a memory of microcomputer 48.

As described above, the spectral reflectance of sample 3 can be calculated under conditions of illumination close to perfect diffusion, by virtue of which errors between units can be reduced.

These coefficients may be determined so that each unit's luminous intensity is identical to that of a certain measurement device, and not so that it simply approximates the luminous intensity of perfect diffusion. In such a case, units of even different models can exhibit equal diffusion by virtue of calculation: therefore, measurement data obtained from measuring devices of different models are not wasted, and the compatibility of data is improved.

Figure 3:
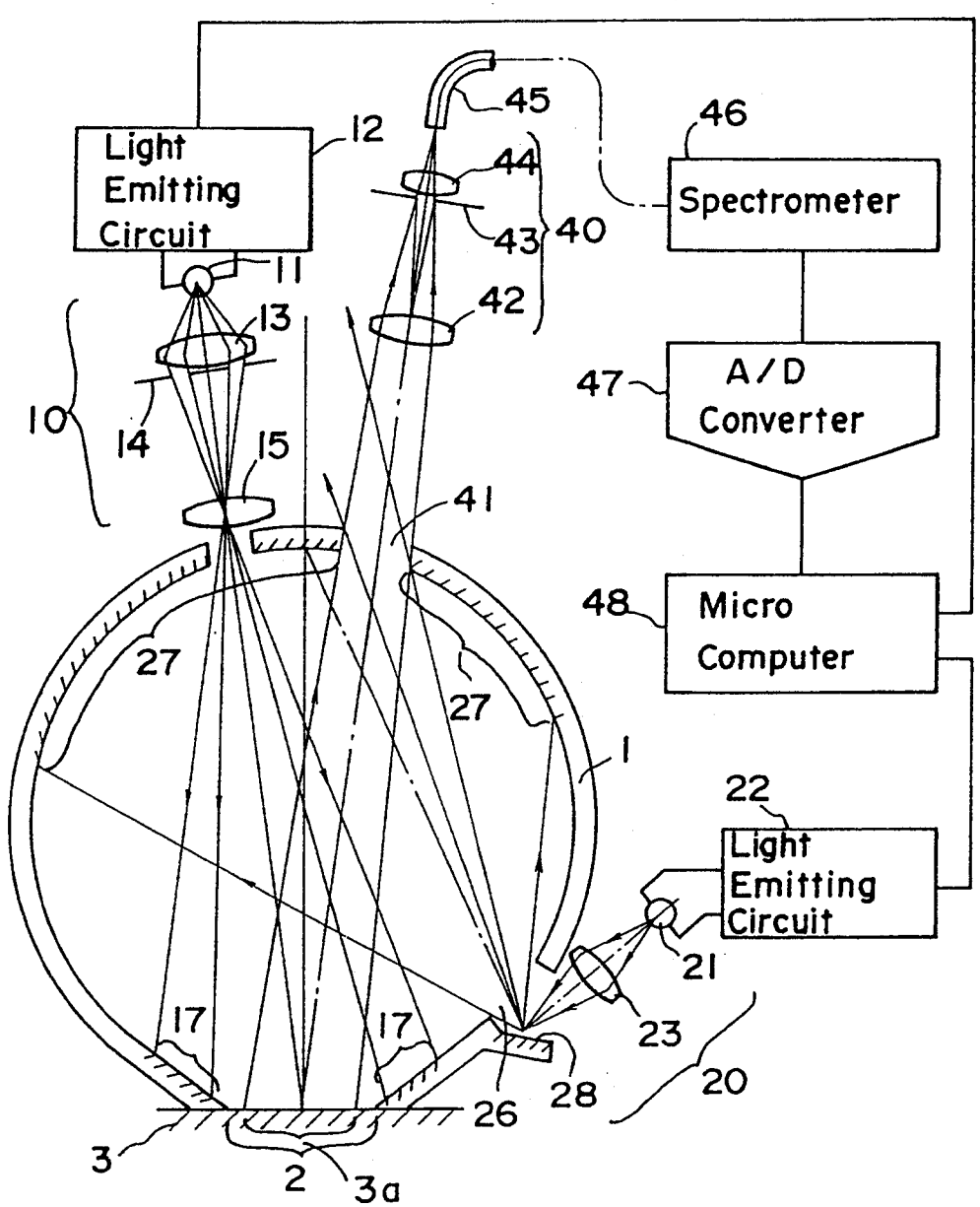
FIG. 3 is an illustration showing the construction of the second embodiment of the device for measuring optical properties of samples of the present invention.
Figure 4:
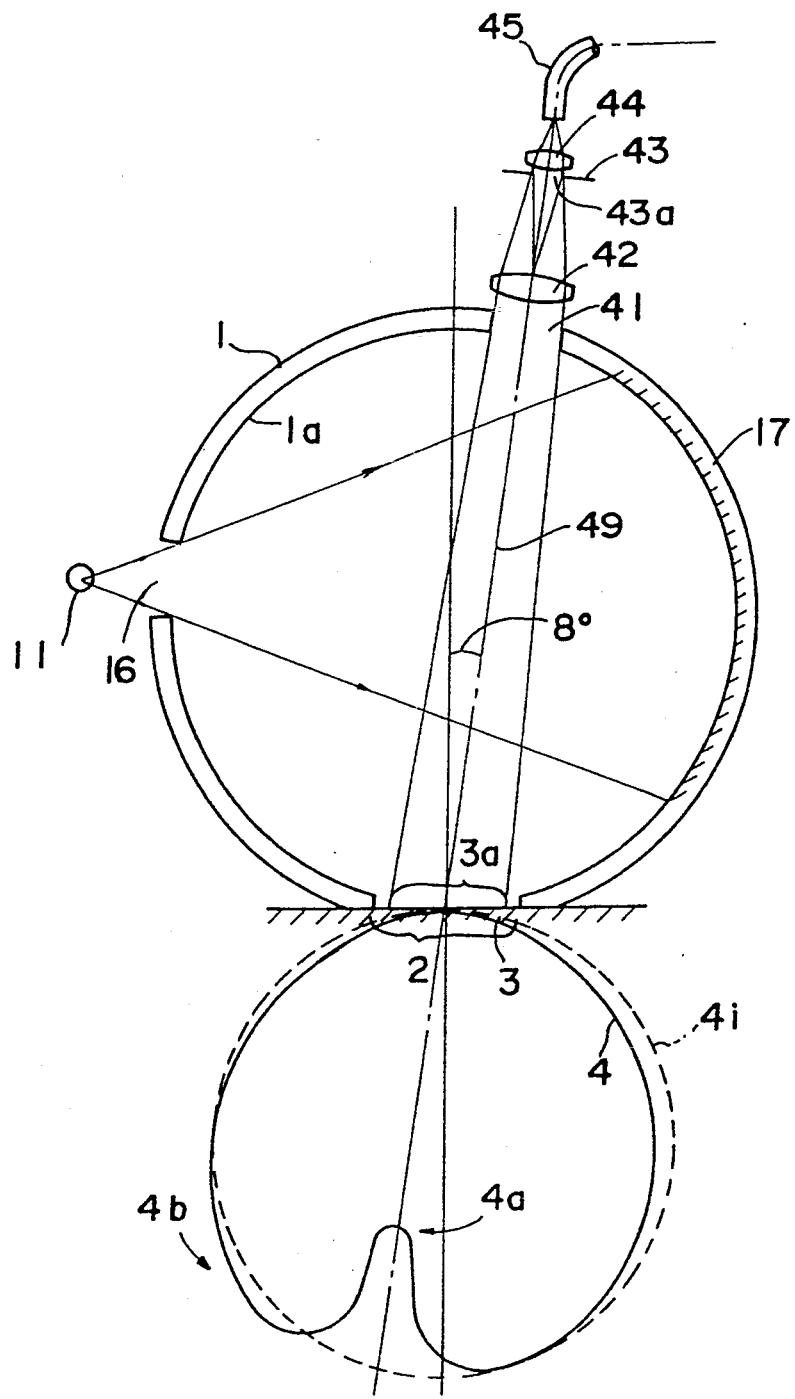
FIG. 4 is an illustration showing the construction and the luminous intensity with regard to a conventional device for measuring optical properties of samples.

Next, the second embodiment of the device for measuring optical properties of samples of the present invention is described with reference to FIG. 3. The same numbers are used for the same components as in the first embodiment, and their explanations are omitted.

This embodiment tries to bring the diffusion of integrating sphere 1 closer to perfect diffusion.

In integrating sphere 1, directly illuminated area 17 near aperture 2 illuminated by first illumination optical system 10 is formed in a tapered shape instead of in a spherical shape. Therefore, with regard to the luminous intensity at aperture 2, light incident at narrow angles is further emphasized in comparison to the luminous intensity in connection with first illumination optical system 10 in the first embodiment shown in FIG. 2A.

Supplemental diffusion plate 28 is formed outside integrating sphere 1 by extending one end of aperture 26, and the light beam from light source 21 forms an image on supplemental diffusion plate 28 via lens 23. The light beam from light source 21 of second illumination optical system 20 forms an image on supplemental diffusion plate 28, after which it is diffused and reflected by supplemental diffusion plate 28 and enters integrating sphere 1.

Therefore, the upper surface of inner wall 1a of integrating sphere 1 becomes widely illuminated, and thus directly illuminated area 27 is formed over a larger area. As a result, with regard to the luminous intensity at aperture 2, light incident at wide angles is reduced in comparison with the luminous intensity in connection with second illumination optical system 20 in the first embodiment shown in FIG. 2B, thereby further nearing perfect diffusion.

Because in this embodiment measurement optical system 40 is located at a distance from integrating sphere 1, and the direct reflected light from supplemental diffusion plate 28 does not directly illuminate aperture 41, there is no effect on measurement optical system 40.

Incidentally, this invention is not limited to the measurement of the sample's reflection, but may be applied to the measurement of transmittance as well.

What is claimed is:

1. A device for measuring optical properties of samples, the device comprising:
   an integrating sphere having an aperture where the sample is placed and multiple apertures to take in the light from light sources;
   multiple light sources placed at said multiple apertures, to illuminate the inside of said integrating sphere;
   a light receiving means to receive light from the sample placed at the sample placement aperture;
   control means to cause said multiple light sources to emit light in sequence;
   multiple storing means to save the output of said light receiving means at each emission of light;
   a means to generate weighting coefficients which convert a sum of luminous intensities of said multiple light sources into an ideal luminous intensity at the sample placement aperture; and
   a means to calculate optical properties of the sample based on the output saved in said multiple storing means and the weighting coefficients generated by said generating means.

2. The device claimed in claim 1, wherein the following condition is met:

$$w_1 F_1 + w_2 F_2 + \ldots + w_i F_i + \ldots + w_n F_n = F_{ideal}$$

where
   $w_1 \ldots w_n$: weighting coefficients generated by said generating means
   $F_1 \ldots F_n$: luminous intensities of said multiple light sources
   $F_{ideal}$: ideal luminous intensity.

3. The device claimed in claim 2, wherein the optical property of the sample is calculated as follows:

$$R = w_1 R_1 + w_2 R_2 + \ldots + w_i R_i + \ldots + w_n R_n$$

where
   R: optical property to be calculated
   $R_1 \ldots R_n$: output of light receiving means at each emission of light, which is saved in said storing means, 4. The device claimed in claim 1, wherein the optical property calculated by said calculating means is spectral transmittance or spectral reflectance.

5. The device claimed in claim 1, wherein said multiple light sources are xenon flashes.

6. A device for measuring optical properties of samples, the device comprising:
   an integrating sphere having a first aperture to place a sample at the bottom, a second aperture to take in light from a light source at the top, and a third aperture to take in light from another light source near the first aperture;
   a first light source placed at the second aperture to illuminate the bottom of the inside of said integrating sphere;
   a second light source placed at the third aperture to illuminate the top of the inside of said integrating sphere;

a light receiving means to receive light from the sample placed at the first aperture;

control means to cause said first and second light sources to emit light in sequence;

a first storing means to save a first output of said light receiving means at emission of light of said first light source;

a second storing means to save a second output of said light receiving means at emission of light of said second light source;

a means to generate weighting coefficients which convert a sum of luminous intensities of said first and second light sources into an ideal luminous intensity at the first aperture; and a means to calculate optical properties of the sample based on the first and second output saved in said first and second storing means and the weighting coefficients generated by said generating means.

7. The device claimed in claim 6, wherein the following condition is met:

$$w_1 F_1 + w_2 F_2 = F_{ideal}$$

where $w_1$, $w_2$: weighting coefficients generated by said generating means $F_1$, $F_2$: luminous intensities of said first and second light sources $F_{ideal}$: ideal luminous intensity.

8. The device claimed in claim 7, wherein the optical property of the sample is calculated as follows:

$$R = w_1 R_1 + w_2 R_2$$

where

R: optical property to be calculated $R_1$, $R_2$: first and second output of light receiving means at each emission of light saved in said first and second storing means.

9. A device for measuring optical properties of samples, the device comprising:

an integrating sphere having an aperture where the sample is placed and multiple apertures to take in light from xenon flashes;

multiple xenon flash devices placed at multiple apertures, to illuminate the inside of said integrating sphere with xenon flashes;

an optical sensor to receive light from the sample placed at the sample placement aperture; and a calculator to calculate optical properties of the sample based on the output of said optical sensor.

10. The device claimed in claim 9, further comprising a generator to generate weighting coefficients which convert a sum of luminous intensities of said multiple xenon flashes into an ideal luminous intensity at the sample placement aperture.

11. The device claimed in claim 10, wherein the luminous intensities of said multiple xenon flashes differ from one another.

12. The device claimed in claim 9, further comprising:

an emitting device to cause said multiple xenon flash devices to emit light; and multiple memories to store the output of the optical sensor for each emission of a xenon flash, wherein said calculator calculates the optical properties based on the output stored in said memories.

13. The device claimed in claim 9, wherein the optical property calculated by said calculator is spectral transmittance or spectral reflectance.

14. A device for measuring optical properties of samples, the device comprising:

an integrating sphere having an aperture where the sample is placed and multiple apertures to take in the light from light sources;

multiple light sources placed at said multiple apertures, to illuminate the inside of said integrating sphere;

an optical sensor to receive light from the sample placed at the sample placement aperture;

a controller to cause said multiple light sources to emit light in sequence;

multiple memories to store the output of said optical sensor at each emission of light;

a generator to generate weighting coefficients which convert a sum of luminous intensities of said multiple light sources into an ideal luminous intensity at the sample placement aperture; and a calculator to calculate optical properties of the sample based on the output stored in said multiple memories and the weighting coefficients generated by said generator.

15. A device for measuring optical properties of samples, the device comprising:

an integrating sphere having a first aperture to place a sample at the bottom, a second aperture to take in light from a light source at the top, and a third aperture to take in light from another light source near the first aperture;

a first light source placed at the second aperture to illuminate the bottom of the inside of said integrating sphere;

a second light source placed at the third aperture to illuminate the top of the inside of said integrating sphere;

an optical sensor to receive light from the sample placed at the first aperture;

a controller to cause said first and second light sources to emit light in sequence;

a first memory to store a first output of said optical sensor at emission of light of said first light source;

a second memory to store a second output of said optical sensor at emission of light of said second light source;

a generator to generate weighting coefficients which convert a sum of luminous intensities of said first and second light sources into an ideal luminous intensity at the first aperture; and a calculator to calculate optical properties of the sample based on the first and second outputs stored in said first and second memories and the weighting coefficients generated by said generator.

* * * * *